(12) United States Patent
Miller et al.

(10) Patent No.: US 9,617,249 B2
(45) Date of Patent: Apr. 11, 2017

(54) BENZOHETEROCYCLIC ANTI-BACTERIAL AGENTS

(71) Applicant: UNIVERSITY OF NOTRE DAME DU LAC, Notre Dame, IN (US)

(72) Inventors: Marvin J. Miller, Notre Dame, IN (US); Garret C. Moraski, Notre Dame, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 0 days.

(21) Appl. No.: 13/753,356

(22) Filed: Jan. 29, 2013

(65) Prior Publication Data

US 2013/0143841 A1  Jun. 6, 2013

Related U.S. Application Data

(63) Continuation of application No. 12/995,437, filed as application No. PCT/US2009/045737 on May 29, 2009, now Pat. No. 8,362,268.

(60) Provisional application No. 61/057,282, filed on May 30, 2008.

(51) Int. Cl.

| A61K 31/4184 | (2006.01) |
| C07D 405/04 | (2006.01) |
| C07D 409/04 | (2006.01) |
| C07D 413/04 | (2006.01) |
| C07D 417/04 | (2006.01) |
| C07D 307/71 | (2006.01) |
| C07D 471/04 | (2006.01) |
| C07F 7/10 | (2006.01) |

(52) U.S. Cl.
CPC ........ *C07D 405/04* (2013.01); *A61K 31/4184* (2013.01); *C07D 307/71* (2013.01); *C07D 409/04* (2013.01); *C07D 413/04* (2013.01); *C07D 417/04* (2013.01); *C07D 471/04* (2013.01); *C07F 7/10* (2013.01)

(58) Field of Classification Search
CPC ................................................ A61K 31/4184
See application file for complete search history.

(56) References Cited

U.S. PATENT DOCUMENTS

| 3,155,571 A | 11/1964 | Sarett et al. |
| 3,309,378 A | 3/1967 | Dunn |
| 3,322,783 A | 5/1967 | Dunn |
| 4,189,589 A | 2/1980 | Meyer et al. |
| 4,772,600 A | 9/1988 | Tomczuk et al. |
| 4,925,853 A | 5/1990 | Smith et al. |
| 5,037,842 A | 8/1991 | Goldstein |
| 6,180,625 B1 | 1/2001 | Persson et al. |
| 6,696,437 B1 | 2/2004 | Lubisch et al. |

| 2005/0026174 A1 | 2/2005 | Dervan et al. |
| 2008/0153837 A1 | 6/2008 | Maillet et al. |
| 2010/0168084 A1 | 7/2010 | Huber et al. |

FOREIGN PATENT DOCUMENTS

| CN | 101434601 A | 5/2009 |
| CN | 101619058 A | 1/2010 |
| EP | 252028 A1 | 1/1988 |
| EP | 0711768 A1 | 5/1996 |
| GB | 1016365 A | 1/1966 |
| GB | 1094903 | 12/1967 |
| JP | 02-306916 A | 3/1999 |
| JP | 2000-280621 A | 10/2000 |
| WO | WO 95/32960 A1 | 12/1995 |
| WO | WO 2006/114272 A1 | 11/2006 |
| WO | WO 2008/019309 A1 | 2/2008 |
| WO | WO 2010/014794 A1 | 2/2010 |

OTHER PUBLICATIONS

De Meo et al., Farmaco (1989), 44(5), pp. 475-482.*
An English translation of De Meo et al. {Farmaco (1989), 44(5), pp. 475-482.*
Chemical Abstracts Registry No. 331712-21-1, indexed in the Registry file on STN CAS ONLIN Apr. 17, 2001.
Ambacheu et al., "Chemistry of 2-substituted benimidazoles. 1.5-Amino-2-methyl(aryl,arylalkyl,pyridyl) benzimidazoles," Chemistry of Heterocyclic Compounds (2000) 36 (4): 421-428.
Bistocchi et al., "Nouveaux derives hetercycliques du benzimidazole a activite germicide (New heterocyclic deriviateives of benimidazole has germicidal activity)," Farmaco, Edizione Scientifica (1982) 37 (9): 597-611.
Burch, H.A., "Nitrofuryl heterocycles, IV, 4-amino-2-(5-nitro-2-furyl)Quinazoline derivatives," Journal of Medicinal Chemistry (1966) 9: 408-410.
Dang et al., "Fructose-1,6-bisphosphatase inhibitors. 2. Design, synthesis, and structure-activity relationship of a series of phosphonic acid containing benzimidazoles that function as 5'-adenosinemonophosphate (AMP) mimics," Journal of the American Chemical Society (2010) 53 (1): 441-451.
El'Chaninov et al., "Reaction of 2-heteroarylbenzimidazole with electrophillic reagents," Chemistry of heterocyclic compounds (1979) 15: 856-858.
Erion et al., "Structure-guiden design of AMP mimics that inhibit fructose-1,6-biphosphatase with high affinity and specificity," Journal of the American Chemical Society (2007) 129: 15480-15490.
Gromachevskaya et al., "Research on 4H-3,1 benzoxazines, 9.*2-alkyl(aryl,furyl)-4H-3,1-benzoxazinium perchlorates and their transformations," Chemistry of Heterocyclic Compounds (1993) 29 (4): 465-468.
Kozlovskaya, I.N., Syntheses based on furancarboxylic acid amides, Chemistry of Heterocyclic Compounds (1989) 25 (11): 1220-1223.

(Continued)

*Primary Examiner* — Laura L. Stockton
(74) *Attorney, Agent, or Firm* — Neifeld IP Law, P.C.

(57) ABSTRACT

Embodiments herein provide compounds and methods of making and using such compounds for prevention and treatment of multidrug resistant bacteria. In particular, embodiments are directed to anti-bacterial agents from benzo[d]heterocyclic scaffolds for prevention and treatment of multidrug resistant bacteria.

4 Claims, 10 Drawing Sheets

(56) References Cited

OTHER PUBLICATIONS

Luo et al., "Design, synthesis, and antiviral properties of 2-aryl-1H-benzimidazole-4-carboxamide derivatives," Frontiers of Chemical Engineering in China (2009) 3 (3): 305-309.

Zhang et al., "Design, synthesis, and biological activity of some novel benzimidazole derivatives against coxsackie virus B3," Chinese Chemical Letters (2009) 20: 921-923.

Pedini et al., "New heterocyclic derivatives of menzimidazole with germicidal activity—XII—Synthesis of N1-glycosyl-2-furyl benzimidazoles," Farmaco (1994) 94 (12): 823-827.

Sasaki et al., "Studies on heteroarmoaticity. XVI. Further studies on the thermal 1,3-dipolar cycloaddition reactions of some aromatic hydroxamoyl chlorides," Bulletin of the Chemical Society of Japan (1968) 41 (9): 2206-2210.

Tomczuk et al., "2-Phenyl-3H-imidazo[4,5-b]pyridine-3-acetamides as non-benzodiazepine anticonvulsants and anxiolytics," Journal of Medicinal Chemistry (1991) 34: 2993-3006.

Xue et al., "Inhibitory properties of 2-substituent-1H-benzimidazole-4-carboxamide derivatives against enteroviruses," Bioorganic & Medicinal Chemistry (2011) 19: 2641-2649.

Zhang et al., "Synthesis of novel benzimidazole derivatives and their antiviral activity against coxsackie virus B3," Chinese Journal of Pharmaceuticals (2009) 40 (7): 488-492.

Pedini et al., "New heterocyclic derivatives of menzimidazole with germicidal activity—XI—experimental validation of QSAR prediction on acntibacterial and antimycotic activity of benzimidazole derivatives," Il Farmaco (1994) 49 (10): 671-674.

Chemical Abstracts Registry No. 3878-19-1, Indexed in the Registry file on STN on Nov. 16, 1984.

Chemical Abstracts Registry No. 3878-18-0, Indexed in the Registry file on STN on Nov. 16, 1984.

Chemical Abstracts Registry No. 2276-61-1, Indexed in the Registry file on STN on Nov. 16, 1984.

Dunn et al., "Antiparasitic agents. I. 2-(nitro-heterocyclic) benzimidazoles, benzoxazoles, and benzothiazoles," Journal of Medicinal Chemistry (1996) 9 (5): 751-753.

Agrawal et al., "Tumor localizing agents. Radioactive iodofluorenaminesulfonic acids," Journal of Medicinal Chemistry (1996) 9 (5): 729-732.

Camacho et al., "Synthesis and biological evaluation of benzimidazole-5-carbohydrazide derivatives as antimalarial, cytotoxic and antitubercular agents," Bioorganic & Medicinal Chemistry (2011) doi: 10.1016/j.bmc.2011.01.050: 1-7.

Pozharskii et al., "Synthesis of 2-(5'-nitro-2'-furyl) benzimidazoles," Chemistry of Heterocyclic Compounds (1969) 5 (1): 139-140.

Pedini et al., "New heterocyclic derivatives of benzimidazole with germicidal activity—VII—2-(5'-nitro-2'-furyl or 2'-thienyl) benzimidazoles with different substituents in the 5-position," Il Farmaco (1990) 45 (3): 303-312.

* cited by examiner

| Compound | | Bacillus subtilis 6633 | E.coli SG 458 | Pseud. Aeruginosa K 799/61 | Pseud. aeruginosa K 799/WT | Staph. aureus 134/94 | Enteroc. faecalis 1528 | Mycobac. smegmatis SG 987 | Mycobac. aurum SB 66 | Mycobac. vaccae 10670 | Mycobac. fortuitum Borstel |
|---|---|---|---|---|---|---|---|---|---|---|---|
| 3a | ND-006422 | 0.5 | 4 | 125 | >62.5 | 8 | 15.6 | 125 | 62.5 | 62.5 | 125 |
| 3b | ND-007651 | 8 | 31.3 | 250 | >62.5 | 62.5 | 1000 | 125 | 500 | 125 | 125 |
| 3c | ND-007877 | 4 | 8 | >250 | >250 | 15.6 | 599 | NT | 250 | 62.5 | NT |
| 3d | ND-007878 | 8 | 4 | 31.3 | 62.5 | 8 | 62.5 | NT | 62.5 | 15.6 | 31.5 |
| 3e | ND-007908 | NT | NT | NT | NT | >64 | NT | NT | 1000 | NT | NT |
| 3f | ND-007900 | 2 | 8 | 31.3 | 62.5 | 8 | 31.3 | NT | 15.6 | 15.6 | 31.3 |
| 3g | ND-007901 | >1 | 4 | 125 | >250 | 4 | 8 | 62.5 | NT | 31.3 | 125 |
| 6a | ND-007573 | NT | NT | NT | NT | >64 | NT | NT | NT | NT | NT |
| 6b | ND-007647 | NT | NT | NT | NT | >64 | NT | NT | NT | NT | NT |
| 10a | ND-007570 | NT | 1000 | 250 | NT | 250 | 1000 | 500 | 500 | 500 | 500 |
| 11a | ND-007571 | NT | 250 | <1 | NT | >2000 | 1000 | >2000 | >2000 | 1000 | >2000 |
| 11b | ND-007652 | NT | >2000 | >2000 | NT | >2000 | >2000 | 1000 | 2000 | 2000 | 500 |
| | ND-007572 | NT | 500 | 250 | NT | 8 | 500 | 125 | 250 | 125 | 62.5 |
| | Ciproflox-acin | | 0.1 | 0.05 | | 25 | 0.8 | 0.8 | 0.1 | 0.4 | 0.1 |

FIGURE 4

| Compound ID | Structure | Mol Wt | Formula |
|---|---|---|---|
| ND-006422 | 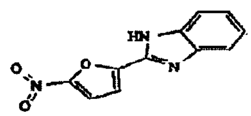 | 229.19 | $C_{11}H_7N_3O_3$ |
| ND-007570 | 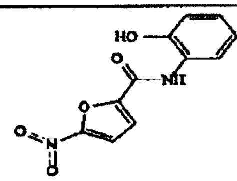 | 248.19 | $C_{11}H_8N_2O_5$ |
| ND-007571 | 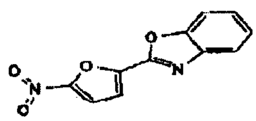 | 230.18 | $C_{11}H_6N_2O_4$ |
| ND-007572 | 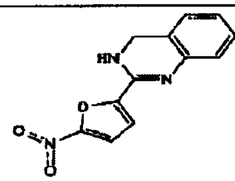 | 243.22 | $C_{12}H_9N_3O_3$ |
| ND-007573 | 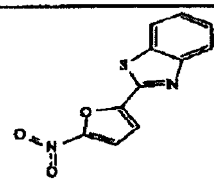 | 246.24 | $C_{11}H_6N_2O_3S$ |
| ND-007647 | 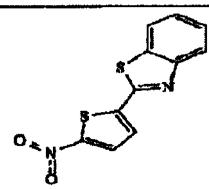 | 262.31 | $C_{11}H_6N_2O_2S_2$ |
| ND-007651 | 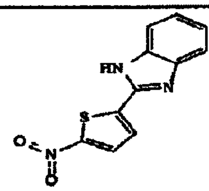 | 245.26 | $C_{11}H_7N_3O_2S$ |

FIGURE 5

| ND-007652 | | 246.24 | $C_{11}H_6N_2O_3S$ |
|---|---|---|---|
| ND-007877 | | 263.64 | $C_{11}H_6ClN_3O_3$ |
| ND-007878 | | 247.18 | $C_{11}H_6FN_3O_3$ |
| ND-007900 | | 243.22 | $C_{12}H_9N_3O_3$ |
| ND-007901 | | 245.19 | $C_{11}H_7N_3O_4$ |
| ND-007908 | | 273.2 | $C_{12}H_7N_3O_5$ |

FIGURE 5
(continued)

| R1 | X | Y | R2 | MRSA MIC (µM) |
|---|---|---|---|---|
| NO₂ | O | NH | H | 8 |
| NO₂ | O | NHCH₂⁻ | H | 8 |
| NO₂ | O | NHCH₃ | H | 31.5 |
| NO₂ | O | NH | 5-F | 8 |
| NO₂ | O | NH | 5-Cl | 15.6 |
| NO₂ | O | NH | 5-CO₂H | >62.5 |
| NO₂ | O | NH | 5-CO₂CH₃ | >62.5 |
| NO₂ | O | NH | 7-CH₃ | 8 |
| NO₂ | O | NH | 7-OH | 4 |
| NO₂ | O | S | H | >62.5 |
| NO₂ | O | O | H | >62.5 |
| NO₂ | S | NH | H | >62.5 |
| NO₂ | S | S | H | >62.5 |
| NO₂ | S | O | H | >62.5 |
| NO₂ | S | NH | 5-Cl | 15.6 |
| 4-OCH₃-Ph | S | NH | 5-F | >62.5 |
| NO₂ | O | NH | 5-CN | 8 |
| NO₂ | S | NH | 7-OH | 15 |
| NO₂ | S | NH | 7-CH₃ | 123 |
| NO₂ | O | NBn | 7-OBn | 150 |
| NO₂ | O | NBz | 7-NBz | 18 |
| NO₂ | O | NH | 5-(C=NH)NH₂ | >62.5 |
| NO₂ | O | NH | 7-OCOCH₃ | 7 |
| NO₂ | O | NBoc | 7-OBoc | 9 |
| NO₂ | O | NH | 7-OTBDMSi | >62.5 |
| NO₂ | O | N-cyclopropyl-carboxyl | 7-OTBDMSi | 9 |
| NO₂ | O | NH | 7-OCH₃ | 9 |
| H | O | NH | H | >62.5 |
| Br | O | NH | H | >62.5 |
| SO₃H | O | NH | H | >62.5 |

| R1 | X | Y | A, B, C, D, R2 | MRSA MIC (μM) |
|---|---|---|---|---|
| NO₂ | O | NH | A=N; B-D = CH; R₂ = 5-Cl | 30 |
| NO₂ | O | NH | D = N; A-C = CH; R₂ = H | 17 |
| NO₂ | O | NH | C = N; A,B,D = CH; R₂ = H | 35 |

MRSA STRAIN PANEL

| | MIC (μg/mL) | |
|---|---|---|
| Strain | ND-7901 | Van. Control |
| ATCC 33591 | 2 | 1 |
| BK2384 | 1 | 1 |
| BSA643 | 1 | 1 |
| BSA678 | 1 | 1 |
| NY2746 | 2 | 1 |
| ACH-0231 | 2 | 2 |
| ACH-0232 | 2 | 1 |

GRAM-POSITIVE STRAINS

| | | MIC (µg/mL) | |
|---|---|---|---|
| Organism | Strain | ND-7901 | Cipro. Control |
| S. aureus COL (MR) | ACH-0011 | 1 | 0.5 |
| S. epidermidis (MS) | SE42 | 1 | 0.25 |
| S. haemolyticus (MS) | ACH-0013 | 0.5 | 8 |
| E. faecalis | ATCC 29212 | 1 | 1 |
| E. faecium | ATCC 49032 | 4 | 8 |
| S. epidermidis | ACH-0082 | 4 | 64 |
| E. faecalis (VR) | ATCC 700802 | 1 | 0.5 |
| E. faecium (VR) | ATCC 700221 | 4 | >64 |

FIGURE 9

GRAM-NEGATIVE STRAINS

| | | MIC (µg/mL) | |
|---|---|---|---|
| Organism | Strain | ND-7901 | Cipro. Control |
| E. cloacae | ACH-0008 | 4 | 0.03 |
| K. pneumoniae | ATCC 13883 | 8 | 0.06 |
| S. marcescens | ACH-0009 | 16 | 0.06 |
| S. typhimurium | ATCC 14028 | 4 | 0.03 |
| A. baumannii | ATCC 9957 | >64 | 2 |
| E. coli | 1GC2 | 16 | 0.5 |
| E. coli | FQR 362265 | 4 | 16 |
| P. aeruginosa | FQR 467296 | >64 | 8 |
| S. maltophila | ATCC 13637 | >64 | 0.25 |

FIGURE 10

MIC/MBC

| Organism | Strain | ND-7901 – MIC (µg/mL) | ND-7901 – MBC (µg/mL) |
|---|---|---|---|
| S. aureus | ATCC 33591 | 2 | 2 |
| S. aureus | BSA643 | 1 | 2 |
| S. epidermidis | SE42 | 1 | 1 |
| S. haemolyticus | ACH-0013 | 0.5 | 0.5 |
| E. faecium | ATCC 49032 | 4 | 4 |
| E. faecalis | ATCC 700802 | 1 | >4 |

SPONTANEOUS RESISTANCE PROFILE

| Organism | Strain | ND-7901 Spontaneous Resistance Frequency |
|---|---|---|
| S. aureus (MSSA) | ATCC 29213 | $<2.6^{-10}$ (n=2) |
| S. aureus (MRSA) | ATCC 700699 | $<6.4^{-10}$ (n=1) |
| S. aureus (MRSA) | ATCC 33591 | $<2.8^{-10}$ (n=1) |

FIGURE 13

RESITANCE VIA SERIAL PASSAGE

| Organism | Strain | MIC (µg/mL) | | | |
|---|---|---|---|---|---|
| | | ND-7901 | CIP | ERM | TET |
| S. aureus | ATCC 29213 | 4 | 0.25 | 1 | 2 |
| S. aureus | 9-1 | 8 | 0.25 | 1 | 1 |
| S. aureus | 9-2 | 16 | 0.25 | 1 | 1 |
| S. aureus | 9-3 | 16 | 0.25 | 1 | 1 |

FIGURE 14

BENZOHETEROCYCLIC ANTI-BACTERIAL AGENTS

CROSS REFERENCE TO RELATED APPLICATIONS

This application is a continuation of U.S. patent application Ser. No. 12/995,437, filed Nov. 30, 2010, which is a continuation of International Application No. PCT/US2009/045737, filed May 29, 2009, which claims priority to U.S. Provisional Patent Application No. 61/057,282, filed May 30, 2008, the entire disclosures of which are hereby incorporated by reference in their entirety.

GOVERNMENT INTERESTS

This invention was made with government support under Grant No. R01 AI 054193 awarded by the National Institutes of Health. The United States Government has certain rights in the invention.

TECHNICAL FIELD

Embodiments herein relate to anti-bacterial agents, and, more specifically, to anti-bacterial agents from benzo[d]heterocyclic scaffolds for prevention and treatment of multidrug resistant bacteria.

BACKGROUND

In 2004, the IDSA (Infectious Disease Society of America) reported that each year 90,000 of the 2 million people who acquire a hospital bacterial infection will die. That is a 4.5% mortality rate arising from just being within the hospital. Multi-drug resistance bacterial strains are a major problem and one that has been increasing very rapidly every year during the last few decades. In brief, from its discovery in 1968 multi-drug resistant *Staphylococcus aureus* (MRSA) had already accounted for greater than 50% of *S. aureus* patient isolates by 1999 in ICUs (intensive care units) within the National Nosocomial Infection Surveillance (NNIS) System. Then by 2003, 59.5% of isolates were from MRSA. Vancomycin resistant enterocci (VRE) has had a similar rapid rise in hospital isolates increasing from its 1990 discovery to 25% of all enterococal isolates in 1999 and then increasing further to 28.3% by 2003 in NNIS surveyed ICUs. Without the immediate discovery of new antibiotics, this rise in multi-drug resistant strains will continue to grow thereby putting everyone treated within hospitals at undue risk of infection and possible death.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 4 illustrates selectivity and potency of various benzimidazoles, benzthiazoles, and benzoxazoles against a panel of microorganisms including gram-positive bacteria, gram-negative bacteria, fungi, yeast, and mycobacteria.

FIG. 5 illustrate the chemical structure, molecular weight, and chemical formula of most of the compounds of FIG. 4.

FIG. 9 illustrates the potency and selectivity of an exemplary compound against a panel of Gram-positive clinical isolate strains compared to a Ciprofloxacin standard in micrograms per milliliter.

FIG. 10 illustrates the potency and selectivity of an exemplary compound against a panel of Gram-negative clinical isolate strains compared to a Ciprofloxacin standard in micrograms per milliliter.

FIG. 13 illustrates a mutational analysis of an exemplary compound by growth of *S. aureus* strains.

FIG. 14 illustrates the mutational analysis of an exemplary compound by serial transfer experiments.

DETAILED DESCRIPTION

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide compounds and methods of making and using such compounds for prevention and treatment of multidrug resistant bacteria.

In embodiments, the aryl or heteroaryl[d]heterocyclic derived compounds show impressive activity against multidrug resistant strains of bacteria including Methicillin-resistant *Staphylococcus aureus* (Methicillin-RSA), Vancomycin-Resistant *Enterococcus* (VRE), and Linezolid-Resistant *Enterococcus* (LRE) infections with potencies near or beyond that of current clinical treatments. In embodiments, these compounds are also effective against *Bacillus subtilis, Escherichia coli, Pseudmonadas aeruginosa, Mycobacterium vaccae, Sporobolomyces salmonicolor, Candida albicans, Penicilluum notatum* and *Mycobacterium tuberculosis* to various extents. Thus, in embodiments, methods of using one or more compounds described herein may be provided for the prevention and/or treatment of multidrug resistant bacteria.

Figure 1:
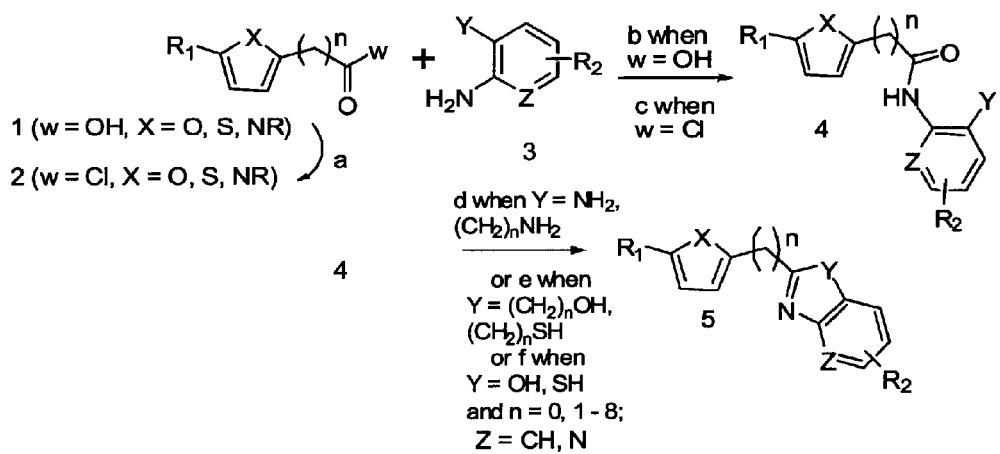
FIG. 1 illustrates a general scheme for the synthesis of various benzo[d]heterocyclic compounds for the treatment of multidrug resistant bacteria in accordance with various embodiments.

In accordance with an embodiment, exemplary compounds may be prepared by the scheme in FIG. 1, which illustrates a general scheme for the synthesis of various benzo[d]heterocyclic compounds for the treatment of multidrug resistant bacteria.

In FIG. 1, reagents include: a) Oxalyl chloride, $CH_2Cl_2$, catalytic N,N-dimethylforamide; b) N-(3-dimethylamino-propyl)-N-ethylcarbodiimide hydrochloride, $Et_3N$, $CH_3CN$; c) $Et_3N$, $CH_2Cl_2$, reflux; d) Acetic acid, reflux; e) (Diethylamino)sulfur trifluoride, $K_2CO_3$, $CH_2Cl_2$, $-78°$ C. to room temp.; and f) p-toluenesulfonic acid, toluene, reflux.

In an embodiment, these compounds may be prepared by an EDC-mediated coupling of 1 or displacement of an acid chloride 2 with 3, base and proper solvent to give an amide 4. Cyclization of the amide 4 with one of the above conditions (depending on Y substituent) results in heterocyclic products 5.

In FIG. 1, compound 3, Y is H, O, SH, $SR_1$, $NH_2$, $NHR_1$, $CH_2NH_2$, $CH_2SH$, $CH_2OH$, $CH_2NHR_1$, $CH_2SR_1$. In FIG. 1, compound 5 may comprise the following: $R_1$ is H, alkyl, substituted alkyl, including halogenated alkyl such as $CF_3$, aryl and substituted aryl, halogen, cycloheteroalkyl (such as morpholine, thiomorpholine, piperazine, piperidine), aryl, heteroaryl, substituted heteroaryl, nitro, sulfone, sulfoxide, sulfamide, phosphate, alkylphosphate (such as $PO(CH_3)_2$, $PO(OCH_3)_2$) boronic acid, or boronic ester; X is O, S, N, or $CH_2$; n=0-8, saturated or unsaturated; Y is O, S, N, or $CH_2$; m=0-3; $R_2$ is H, OH, halogen, amine, COOH, $NHR_1$ (wherein $R_1$ is as previously defined), $NR_1R_1$, alkyl, substituted alkyl, cycloalkyl, or functionalized alkyl (including alkenes, alkynes, alcohols, epoxides, ketones, esters, ethers, aldehydes, nitriles, nitros, thiols, thioesters, sulfides, disulfide, sulfones, sulfoxides, amines, amides, ureas, carbamates), cycloheteroalkyl (such as morpholine, thiomorpholine, piperazine, piperidine), acyl, halogenated acyl, substituted acyl, aryl, substituted aryl, heteroaryl, substituted heteroaryl, heterocyclic (such as furan, nitrofuran, thiophene, nitrothiophene, imidazole, oxazole, oxazoline, thiazole, thiazoline, triazole, pyridine, pyrazine, naphthalene, diketopiperazine, quinoline, isoquinoline, imidazopyridines, oxazolidinone, and all substitutions upon), wherein $R_2$ may be monosubstituted or polysubstituted; and Z is N in the 2, 3, 4, or 5-positions of the phenyl ring and any combination therein (with the 2-position being exemplified by the structure shown).

In embodiments, compounds may be formed as a prodrug to enhance the delivery of the compound, such as enhancing absorption, distribution, metabolism, excretion, etc. Suitable groups to provide a prodrug may, for example, entail modifying an OH group to form an O-prodrug group, wherein the prodrug group is one of acyl, ester, carbamate, urea, sugar, or amino acid.

In embodiments, various molecules as described herein have surprising activity against MRSA. One exemplary compound tested (nitrofuran benzimidazole), showed results against MRSA of (MIC=8 µM) and against VRE (MIC=16 µM). While this particular molecule has been tested previously, the present application is the first disclosure of this compound having activity against multi-drug resistant "super bug" strains. In addition, in accordance with an embodiment described herein, this compound and analogs thereof may be synthesized in high yields in just a single step. Further embodiments herein provide analogs of the afore-mentioned compounds and methods of making and using such compounds.

Figure 2:
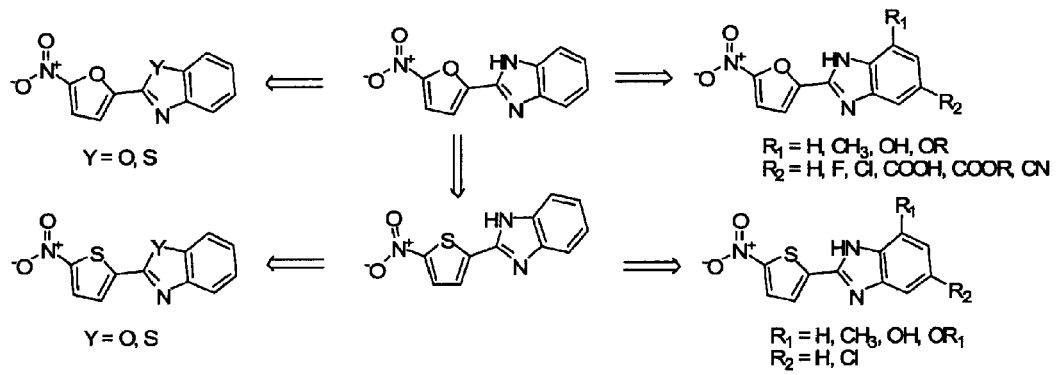
FIG. 2 is a flowchart of initial analogs generated to explore the effects on antibacterial potency and selectivity of nitrofuran replacement with nitrothiophene in accordance with embodiments herein.

In a time of rapid and increasing resistance toward the last line antibacterial agents like Vancomycin and Linezolid, it is prudent that investigation of all new leads undertaken. In an embodiment, a set of analogs (see FIG. 2) were produced in order to explore potency and antimicrobial selectivity. The next generation of benzoxazole and benzthiazole derivatives, as well as the effects of substitution of the benzimidazole core on antibacterial potency and selectivity, were explored.

Figure 3:
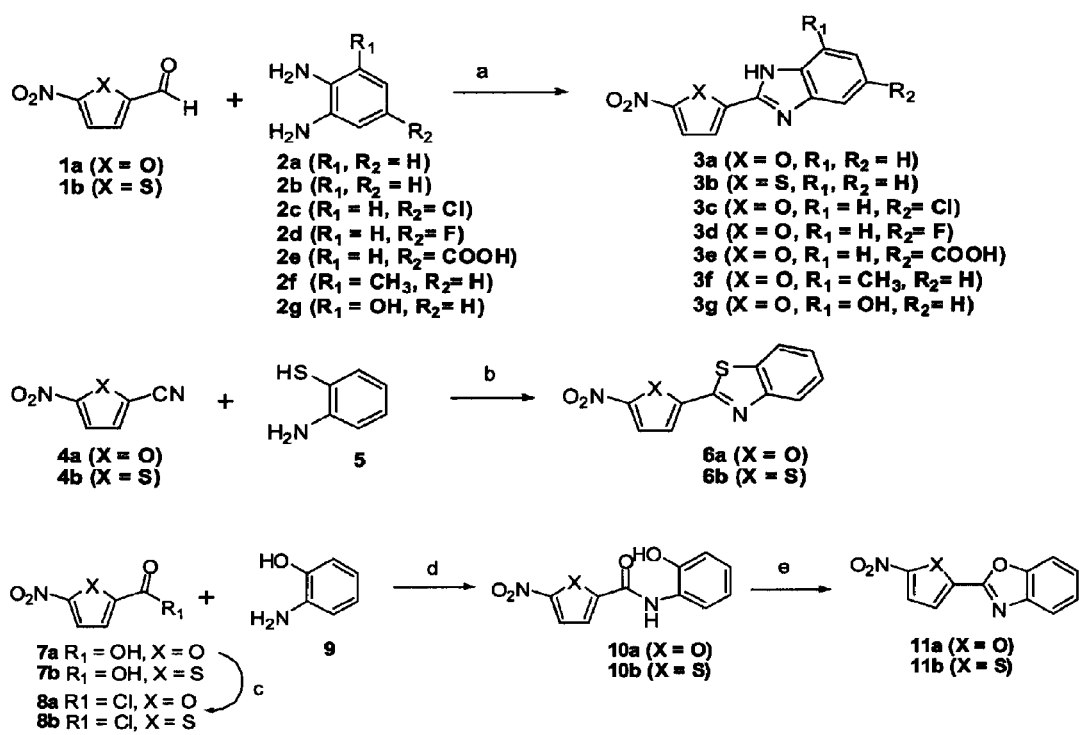
FIG. 3 illustrates specific examples of the syntheses used to make benzimidazoles from aldehydes, benzthiazoles from nitriles, and benzoxazoles from acid chlorides in accordance with embodiments.

Synthesis of analogs was accomplished in a simple straightforward manner as shown in FIG. 3. FIG. 3 illustrates specific examples of the syntheses used to make benzimidazoles from aldehydes, benzthiazoles from nitriles, and benzoxazoles from acid chlorides. Fortuitously, many compounds may be made in a just one step. For instance, condensation of 5-nitro-2-furaldehyde 1 (where X is O) or 5-nitro-2-thiophenealdehyde 1 (where X is S) with various diamines, 2, followed by oxidation with potassium ferricyanide results in a panel of substituted benzimidazoles, 3a to 3g. Next, the benzthiazoles (6a and 6b) may be easily prepared by an acid catalyzed cyclization of nitrile, 4, and 2-aminothiophenol (5). Finally, benzoxazoles (11a and 11b) may be prepared in a two step process involving coupling of easily prepared acid chloride, 8, with 2-aminophenol (9) to give intermediate amide (10) which may then be cyclized with p-toluenesulfonic acid in refluxing toluene.

In FIG. 3, the reagents include: (a) $KFe(CN)_6$, $CH_3OH$, water, reflux, 2 h-16 h; (b) p-TSOH, ethanol, reflux, 16 h; (c) Oxalyl chloride, $CH_2Cl_2$, DMF (drop), 4 h; (d) $Et_3N$, $CH_2Cl_2$, reflux, 16 h; and (e) p-TSOH, toluene, reflux, 16 h.

In accordance with an embodiment, in order to first broadly screen these compounds, an agar diffusion assay was employed to determine whether these compounds have any activity against a diverse array of organisms which include MRSA and VRE. Then to follow up, if a compound showed promise (by having a large zone of inhibition) its minimum inhibition concentration at 90% (MIC) would be determined for that specific organism (FIG. 4). FIG. 4 illustrates selectivity and potency of various benzimidazoles, benzthiazoles, and benzoxazoles against a panel of microorganisms including gram-positive bacteria, gram-negative bacteria, fungi, yeast, and mycobacteria. The minimum inhibition concentration at 90% is shown in micromolar concentration. In an embodiment, the initial agar diffusion assay screen was encouraging as it hinted that many of these compounds have a broad spectrum of activity while others showed some specificity towards specific organisms. Therefore many of the compounds had their MICs determined which reflected many of the findings of the diffusion assay. FIG. 5 illustrates the chemical structure, molecular weight, and chemical formula of most of the compounds of FIG. 4.

Figure 6:
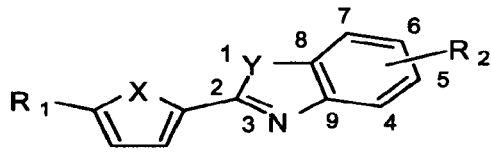
FIG. 6 illustrates the potency of various benzo[d]heterocyclic compounds against methicillin-resistant *Staphylococcus aureus* (MRSA) in micromolar concentration.
Figures 7, 8:
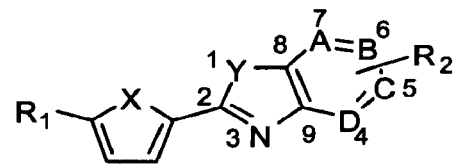
FIG. 7 illustrates the potency of various imidazopyridine compounds against MRSA in micromolar concentration.
FIG. 8 illustrates the potency and selectivity of an exemplary compound against a panel of MRSA clinical isolates compared to a Vancomycin standard in micrograms per milliliter.

FIG. 6 illustrates the potency of various benzo[d]heterocyclic compounds against methicillin-resistant *Staphylococcus aureus* (MRSA) in micromolar concentration. FIG. 7 illustrates the potency of various imidazopyridine compounds against MRSA in micromolar concentration.

All the anhydrous solvents, reagent grade solvents for chromatography and starting materials were purchased from either Aldrich Chemical Co. (Milwaukee, Wis.) or Fisher Scientific (Suwanee, Ga.). General methods of purification of compounds involved the use of silica cartridges purchased from AnaLogix, Inc. (Burlington, Wis.; www.analogix.com) and/or recrystallization. The reactions were monitored by thin-layer chromatography (TLC) on precoated Merck 60 $F_{254}$ silica gel plates and visualized using UV light (254 nm).

All compounds were analyzed for purity and characterized by $^1$H and $^{13}$C NMR using a Varian 300 MHz NMR and Varian 500 MHz NMR spectrometer. Chemical shifts are reported in ppm ($\delta$) relative to the residual solvent peak and coupling constants (J) are reported in hertz (Hz) (s=singlet, bs=broad singlet, d=doublet, dd=double doublet, bd=broad doublet, ddd=double doublet of dublet, t=triplet, tt=triple triplet, q=quartet, and m=multiplet) and analyzed using MestReC NMR data processing.

Mass Spectra values are reported as m/z. All reactions were conducted under Argon unless otherwise noted. Solvents were removed in vacuo on a rotary evaporator. The LC/MS analyses were carried out on Waters ZQ instrument consisting of chromatography module Alliance HT, photodiode array detector 2996, and mass spectrometer Micromass ZQ, using a 3×50 mm Pro C18 YMC reverse phase column. Mobile phases: 10 mM ammonium acetate in HPLC grade water (A) and HPLC grade acetonitrile (B). A gradient was formed from 5% to 80% of B in 10 minutes at 0.7 mL/min. The MS electrospray source operated at capillary voltage 3.5 kV and a desolvation temperature 300° C. Elemental analyses were performed by Midwest Microlabs, LLC (Indianapolis, Ind.). Yields quoted are unoptimized.

Abbreviations: DCM=dichloromethane; DMF=dimethylformamide; ACN=acetonitrile; EtOAc=ethyl acetate; HOAc=acetic acid; EDCI=N-(3-Dimethylaminopropyl)-$N^1$-ethylcarbodiimide hydrochloride; DMAP=4-dimethylaminopyridine; Et$_3$N=triethylamine; and EtOH=ethanol.

The synthesis and testing of an exemplary compound (ND-7901) are detailed below.

filter pad was washed with ethanol. The filtrate liquor and washings were combined and concentrated in vacuo and the residue was recrystallized from EtOH:H$_2$O (80/20 to give 180 mg of 3g as a dark solid (26%) after filtration. $^1$H NMR (300 MHz, DMSO) $\delta$ 7.90 (1 H, m), 7.42 (1 H, m), 7.06 (2 H, m), 6.59 (1 H, m); HRMS calcd. for C$_{11}$H$_7$N$_3$O$_4$, 246.0515 found 246.0504. LC/MS Retention time 4.73 min (>95%), FABMS 246.4 (M+1).

FIG. 8 illustrates the potency and selectivity of ND-7901 against a panel of MRSA clinical isolates compared to a Vancomycin standard in micrograms per milliliter.

FIG. 9 illustrates the potency and selectivity of ND-7901 against a panel of Gram-positive clinical isolate strains compared to a Ciprofloxacin standard in micrograms per milliliter. ND-7901 exhibits good activity against Gram-positive isolates. FIG. 10 illustrates the potency and selectivity of ND-7901 against a panel of Gram-negative clinical isolate strains compared to a Ciprofloxacin standard in micrograms per milliliter. ND-7901 has limited activity against Gram-negative isolates.

Figures 11, 12:
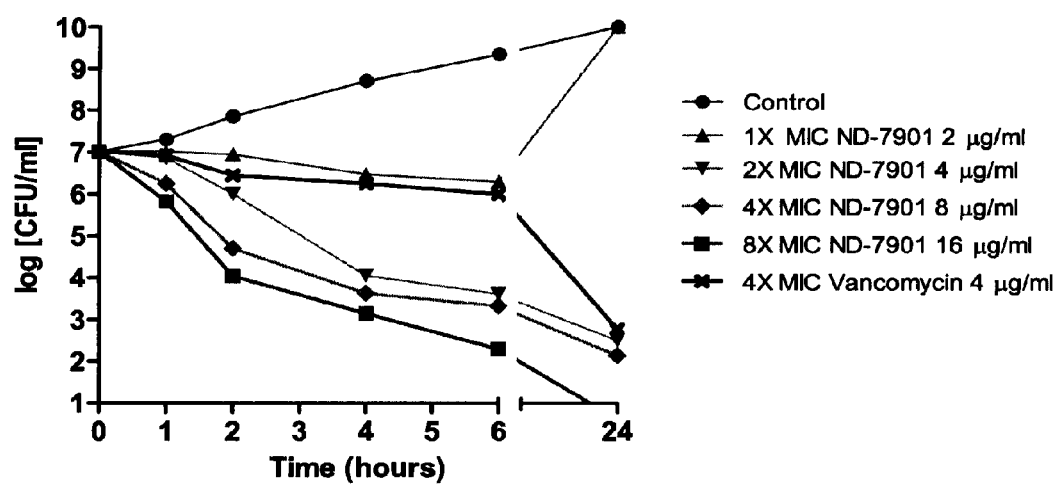
FIG. 11 illustrates the minimum inhibitory concentration (MIC) and the minimum bactericidal concentration (MBC) determinations of an exemplary compound to various Gram-positive strains.
FIG. 12 illustrates results of a time-kill assay of an exemplary compound against a methicillin-sensitive *S. aureus* strain (MSSA).

FIG. 11 illustrates the minimum inhibitory concentration (MIC) and the minimum bactericidal concentration (MBC) determinations of ND-7901 to various Gram-positive strains. A series of broths were mixed with solutions of diluted drug an inoculum was applied. After incubation, the MIC was determined as the first concentration in which the growth of the organism has been inhibited. In contrast, the MBC was measured by inoculating the series of broths used for the MIC determination onto drug-free medium. The MBC is the first dilution at which growth is not observed. ND-7901 is bactericidal against most Gram-positive isolates.

FIG. 12 illustrates results of a time-kill assay of ND-7901 against methicillin-sensitive *S. aureus* (MSSA), ATCC 29213, showing the rapid kinetics of bacteria death when treated with drug at various concentrations with Vancomycin as the control.

FIG. 13 illustrates a mutational analysis of ND-701 by growth of *S. aureus* strains overnight with no selection and recovery of resistant colonies on drug plates at 2-4 times the MIC value. ND-7901 shows very low mutation such that no spontaneous mutants were recovered.

FIG. 14 illustrates the mutational analysis of ND-7901 by serial transfer experiments. As such, the *S. aureus* strains were grown with ND-7901 (0.5-2 times the MIC) added and passed serially until resistance was found. ND-7901 shows a very low level of resistance after 8 passages.

The synthesis and testing of various related compounds are detailed below.

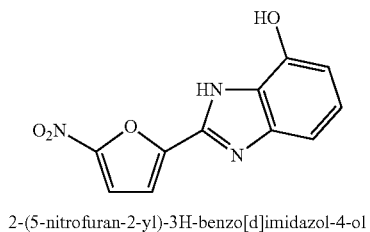 [SMILES: O=[N+]([O-])c1ccc(-c2nc3cccc(O)c3[nH]2)o1]

2-(5-nitrofuran-2-yl)-3H-benzo[d]imidazol-4-ol

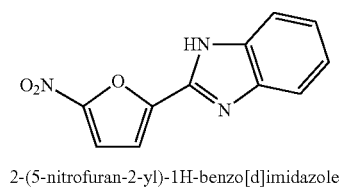 [SMILES: O=[N+]([O-])c1ccc(-c2nc3ccccc3[nH]2)o1]

2-(5-nitrofuran-2-yl)-1H-benzo[d]imidazole

5-Nitro-2-furaldehyde (1a, 401 mg, 2.8 mmol) and 2,3-diaminophenol (2 g, 300 mg, 2.4 mmol) were dissolved in 10 mL of methanol. Next, a 5 mL aqueous solution of potassium ferricyanide (1.7 g, 5.1 mmol) was added and the reaction was heated to reflux for 16 hours while being exposed to air. Then the reaction was cooled, filtered and the 5-Nitro-2-furaldehyde (1a, 1.0 g, 7.0 mmol) and 1,2-phenylenediamine (2a, 658 mg, 6.0 mmol) were dissolved in 15 mL of methanol. Next, an 8 mL aqueous solution of potassium ferricyanide (4.2 g, 12.6 mmol) was added and the reaction was heated to reflux for 3 hours while exposed to air. The reaction was cooled, then filtered and the filter pad was washed with ethanol. The filtrate liquor and washings were combined, concentrated in vacuo and the residue was recrystallized with EtOH:H$_2$O (80/20) to give 1.34 g of 3a as a red-tan solid (83%) after filtration. Mp 225-226° C.; $^1$H NMR (300 MHz, DMSO) δ 7.91 (1 H, d, J=3.9 Hz), 7.66 (2 H, m), 7.48 (1 H, d, J=3.7 Hz), 7.30 (2 H, m); HRMS calcd. For C$_{11}$H$_7$N$_3$O$_3$, 230.0566 found 230.0561. LC/MS Retention time 5.55 min (>95%), FABMS 230.3 (M+1).

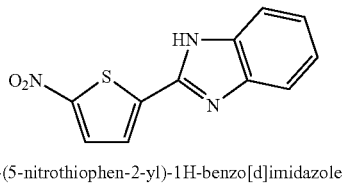

2-(5-nitrothiophen-2-yl)-1H-benzo[d]imidazole

5-Nitro-2-thiophenecarboxyaldehyde (1b, 500 mg, 3.1 mmol) and 1,2-phenylendiamine (2a, 286 mg, 2.6 mmol) were dissolved in 10 mL of methanol. Next, a 5 mL aqueous solution of 1.57 grams of potassium ferricyanide was added and the mixture was heated to reflux for two hours. Then the reaction was cooled, filtered and filter pad was washed with ethanol. The filtrate liquor and washings were combined and concentrated in vacuo and the residue was recrystallized from EtOH:H$_2$O (80/20). A dark tan solid of 3b was collected by filtration, 180 mg (28%). $^1$H NMR (300 MHz, DMSO) δ 8.24 (1 H, d, J=4.4 Hz), 7.84 (1 H, d, J=4.4 Hz), 7.65 (2 H, m), 7.29 (2 H, m); HRMS calcd. for C$_{11}$H$_7$N$_3$O$_2$S, 246.0337 found 246.0324. LC/MS Retention time 6.53 min (<95%), FABMS 244.4 (M−1).

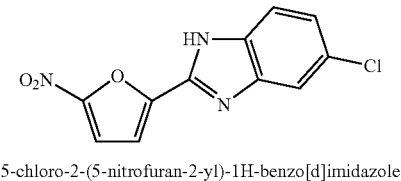 [SMILES: O=[N+]([O-])c1ccc(-c2nc3cc(Cl)ccc3[nH]2)o1]

5-chloro-2-(5-nitrofuran-2-yl)-1H-benzo[d]imidazole

5-Nitro-2-furaldehyde (1a, 304 mg, 2.1 mmol) and 4-chloro-1,2-phenylenediamine (2c, 253 mg, 1.8 mmol) were dissolved in 10 mL of methanol. Next, a 10 mL aqueous solution of potassium ferricyanide (821 mg, 3.2 mmol) was added and the reaction was heated to reflux for 16 hours with exposure to air. The reaction was cooled, then filtered and the filter pad was washed with ethanol. The filtrate liquor and washings were combined and concentrated in vacuo and the residue was recrystallized from EtOH:H$_2$O (80/20) to give 257 mg of 3c as a dark green solid (55%) after filtration. Mp 230-235° C.; $^1$H NMR (300 MHz, DMSO) δ 7.96-7.82 (1 H, bs), 7.76-7.57 (2 H, bs), 7.55-7.43 (1 H, bs), 7.37-7.23 (1 H, bs); HRMS calcd. for C$_{11}$H$_6$ClN$_3$O$_3$, 264.0176 found 264.0189. LC/MS Retention time 7.03 min (>95%), FABMS 264.2 (M+1).

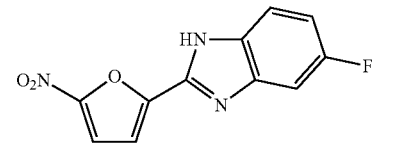

5-fluoro-2-(5-nitrofuran-2-yl)-1H-benzo[d]imidazole

5-Nitro-2-furaldehyde (1a, 310 mg, 2.2 mmol) and 4-fluoro-1,2-phenylyenediamine (2d, 230 mg, 1.8 mmol) were dissolved in 10 mL of methanol. Next, a 10 mL aqueous solution of potassium ferricyanide (837 mg, 3.2 mmol) was added and the reaction was heated to reflux for 3 hours with exposure to air. Then the reaction was cooled, filtered and the filter pad was washed with ethanol. The filtrate liquor and washings were combined and concentrated in vacuo and the residue was recrystallized from EtOH:H$_2$O (80/20) to give 111 mg of 3d as a yellow-green solid (25%) after filtration. Mp 235-240° C.; $^1$H NMR (300 MHz, DMSO) δ 7.96-7.84 (1 H, bs), 7.75-7.60 (1 H, bs), 7.58-7.38 (2 H, bs), 7.27-7.08 (1 H, bs); HRMS calcd. for C$_{11}$H$_6$FN$_3$O$_3$, 248.0471 found 248.0474 found. LC/MS Retention time 6.07 min (>95%), FABMS 248.3 (M+1).

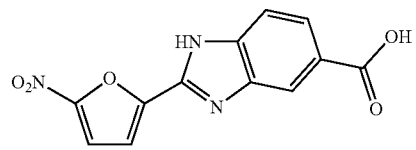

2-(5-nitrofuran-2-yl)-1H-benzo[d]imidazole-5-carboxylic acid

5-Nitro-2-furaldehyde (1a, 306 mg, 2.1 mmol) and 2,3-diaminobenzoic acid (2e, 281 mg, 1.8 mmol) were dissolved in 10 mL of methanol. Next, a 5 mL aqueous solution of potassium ferricyanide (1.3 g, 3.8 mmol) was added and the reaction was heated to reflux for 16 hours while exposed to air. Then the reaction was cooled, filtered and the filter pad was washed with ethanol. The filtrate liquor and washings were combined and concentrated in vacuo and the residue was recrystallized from EtOH:H$_2$O (80/20) to give 512 mg of 3e as a brown solid (88%) after filtration. $^1$H NMR (300 MHz, DMSO) δ 8.22 (1 H, s), 7.88 (1 H, d, J=3.9 Hz), 7.82 (1 H, d, J=8.2 Hz), 7.63 (1 H, d, J=3.9 Hz), 7.56 (1 H, d, J=8.5 Hz); HRMS calcd. for C$_{12}$H$_7$N$_3$O$_5$, 274.0464 found 274.0446. LC/MS Retention time 3.05 min (>95%), FABMS 274.3 (M+1).

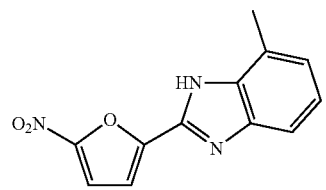

7-methyl-2-(5-nitrofuran-2-yl)-1H-benzo[d]imidazole

5-Nitro-2-furaldehyde (1a, 407 mg, 2.8 mmol) and 2,3-diaminotoluene (2f, 300 mg, 2.4 mmol) were dissolved in 10 mL of methanol. Next, a 5 mL aqueous solution of potassium ferricyanide (1.7 g, 5.1 mmol) was added and the reaction was heated to reflux for 3 hours while exposed to air. The reaction was cooled, then filtered and the filter pad was washed with ethanol. The filtrate liquor and washings were combined and concentrated in vacuo and the residue was recrystallized from EtOH:H$_2$O (80/20) to give 519 mg of 3f as a brown solid (75%) after filtration. $^1$H NMR (300 MHz, DMSO) δ 7.82 (1 H, d, J=3.9 Hz), 7.40 (2 H, m), 7.11 (1 H, t, J=7.6, 7.6 Hz), 7.01 (1 H, d, J=6.8 Hz); HRMS calcd. for C$_{12}$H$_9$N$_3$O$_3$, 244.0722 found 244.0729. LC/MS Retention time 6.32 min (>95%), FABMS 244.4 (M+1).

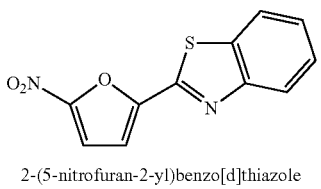 [SMILES: O=[N+]([O-])c1ccc(-c2nc3ccccc3s2)o1]

2-(5-nitrofuran-2-yl)benzo[d]thiazole

5-Nitro-2-furonitrile (4a, 185 mg, 1.3 mmol) was dissolved in 10 mL of ethanol and then the 2-aminothiophenol (5, 0.15 mL, 1.4 mmol) and p-toluenesulfonic acid, monohydrate (240 mg, 1.3 mmol) were added and the reaction was heated to 80° C. overnight. The reaction was concentrated to dryness in vacuo and then the residue was dissolved in EtOAc and washed with 10% sodium bicarbonate (2×), 0.5 N citric acid (2×) and then satd. brine solution. The organic phase was collected and dried over sodium sulfate, filtered and then concentrated in vacuo to give a dark oil. The material was purified through a silica gel column eluting with 100% DCM and product 6a was collected as a yellow-tan solid, 75 mg (24%). $^1$H NMR (300 MHz, DMSO) δ 8.31-8.12 (1H, m), 7.82 (1 H, dd, J=66.5, 4.0 Hz), 7.69-7.53 (1 H, m), 7.48 (1 H, d, J=8.0 Hz), 7.14-7.08 (2 H, m); HRMS calcd. for $C_{11}H_6N_2O_3S$, 247.0177, found 247.0171. LC/MS Retention time 8.07 min (<95%), FABMS 247.2 (M+1).

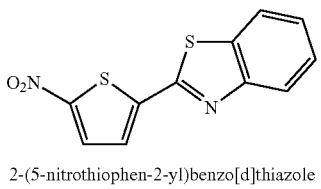 [SMILES: O=[N+]([O-])c1ccc(-c2nc3ccccc3s2)s1]

2-(5-nitrothiophen-2-yl)benzo[d]thiazole

5-Nitro-2-thiophenecarbonitrile (4b, 206 mg, 1.3 mmol) was dissolved in 10 mL of ethanol and then the 2-aminothiophenol (5, 0.15 mL, 1.4 mmol) and p-toluenesulfonic acid, monohydrate (243 mg, 1.3 mmol) were added and the reaction was heated to 80° C. overnight. The reaction was concentrated to dryness in vacuo and the residue was dissolved in EtOAc and washed with 10% sodium bicarbonate (2×), 0.5 N citric acid (2×) and then satd. brine solution. The organic phase was collected, dried over sodium sulfate, filtered and then concentrated in vacuo to give a red oil. The residual material was triturated with dichloromethane and 6b was obtained as red solid after filtration, 125 mg (37%). $^1$H NMR (300 MHz, DMSO) δ 8.22 (1 H, dd, J=2.3, 0.8 Hz), 8.20 (1 H, s), 8.14-8.08 (1 H, m), 7.95 (1 H, dd, J=4.4, 0.8 Hz), 7.64-7.50 (2 H, m); HRMS calcd. for $C_{11}H_6N_2O_2S_2$, 263.9949, found 263.9953. LC/MS Retention time 9.55 min (<95%), FABMS 263.3 (M+1).

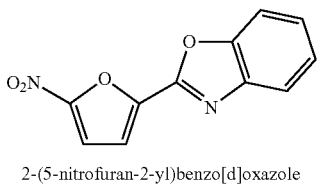

2-(5-nitrofuran-2-yl)benzo[d]oxazole

5-Nitro-2-furoic acid (7a, 1.5 g, 9.4 mmol) was partly dissolved in 20 mL of dry dichloromethane. Oxayl chloride (1.8 mL, 21.3 mmol) was added followed by a few drops of DMF. The reaction was stirred for 4 hours then concentrated to dryness in vacuo to give intermediate acid chloride, 8a, as yellow oil which became solid upon standing, 1.0 g (99%). 5-Nitrofuran-2-carbonyl chloride (8a, 624 mg, 3.5 mmol) was dissolved in 10 mL of anhydrous dichloromethane and the solution was cooled to 0° C. 2-Aminophenol (9, 460 mg, 4.2 mmol) was added followed by Et$_3$N (1.4 mL, 10.5 mmol) and the reaction was then allowed to warm to room temperature and stirred overnight. The reaction was concentrated to dryness in vacuo then diluted with EtOAc (75 mL) and washed with 0.5 N citric acid (2×), 10% sodium bicarbonate soln. (2×) and then satd. brine. The organic phase was dried over sodium sulfate and concentrated in vacuo to give a yellow film. The residual material was triturated with dichloromethane and upon cooling a yellow solid of N-(2-hydroxyphenyl)-5-nitrofuran-2-carboxamide, 10a, was collected, 631 mg (73%). HRMS calcd. for $C_{11}H_8N_2O_5$, 249.0511 found 249.0517. N-(2-Hydroxyphenyl)-5-nitrofuran-2-carboxamide (10a, 151 mg, 0.6 mmol) was dissolved in 6 mL of toluene containing p-toluenesulfonic acid, monohydrate (700 mg, 3.7 mmol) and the reaction was heated to reflux overnight. The reaction was concentrated in vacuo then purified through a silica gel column eluting with dichloromethane and increasing polarity to 10% EtOAc:dichloromethane to collect product 11a as a yellow-green solid, 62 mg (44%). $^1$H NMR (300 MHz, CDCl$_3$) δ 7.87-7.81 (1 H, m), 7.67-7.62 (1 H, m), 7.46 (4 H, m); HRMS calcd. for $C_{11}H_6N_2O_4$, 231.0406 found 231.0423. LC/MS Retention time 7.53 min (<95%), FABMS 231.3 (M+1).

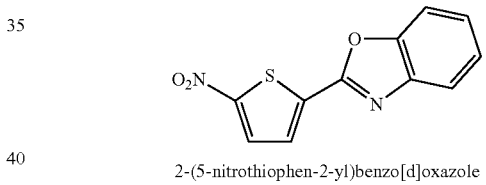

2-(5-nitrothiophen-2-yl)benzo[d]oxazole

2-Nitrothiophene-4-carboxylic acid (7b, 200 mg, 1.1 mmol) was dissolved in 5 mL of dry acetonitrile and then the EDCI (434 mg, 2.2 mmol), DMAP (414 mg, 3.4 mmol) and 2-aminophenol (9, 137 mg, 1.2 mmol) was added. The reaction was stirred at room temperature overnight under argon. The reaction was concentrated in vacuo to dryness then diluted with EtOAc (75 mL) and then the organic phase was washed 2× with 0.5 N citric acid, 2× with aqueous 10% sodium bicarbonate and satd. brine solution. The organic phase was dried over sodium sulfate and concentrated to give a red solid. The residue was triturated with dichloromethane to give product 10b which was collected by filtration, 219 mg (73%). The crude N-(2-hydroxyphenyl)-5-nitrothiophene-2-carboxamide (10b, 219 mg, 0.83 mmol) was dissolved in 6 mL of toluene containing p-toluenesulfonic acid, monohydrate (788 mg, 4.14 mmol) and the reaction was heated to reflux overnight. The reaction was concentrated in vacuo then purified through a silica gel column eluting with a gradient from pure dichloromethane to 5% EtOAc:dichloromethane to give product 11b as an off white solid, 99 mg (49%) after evaporation of the solvent. $^1$H NMR (300 MHz, CDCl$_3$) δ 8.58-8.55 (1 H, m), 8.31 (1 H, d, J=1.78 Hz), 7.80-7.75 (1 H, m), 7.63-7.56 (1 H, m), 7.45-7.36 (2 H, m); $^{13}$C NMR (126 MHz, CDCl$_3$) δ 157.26, 150.41, 141.47, 132.12, 127.02, 125.97, 125.15, 120.37, 110.75; HRMS calcd. for $C_{11}H_6N_2O_3S$, 247.0177, found 247.0177. LC/MS Retention time 8.35 min (<95%), FABMS 247.3 (M+1).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of treating a drug-resistant bacterial strain, comprising:
administering a compound to an individual infected with or suspected of being infected with a methicillin-resistant *Staphylococcus aureus* strain, a vancomycin-resistant *Enterococcus* strain, or a linezolid-resistant *Enterococcus* strain, wherein the bacterial strain is killed or inhibited from growing, wherein the compound is one of the following compounds:

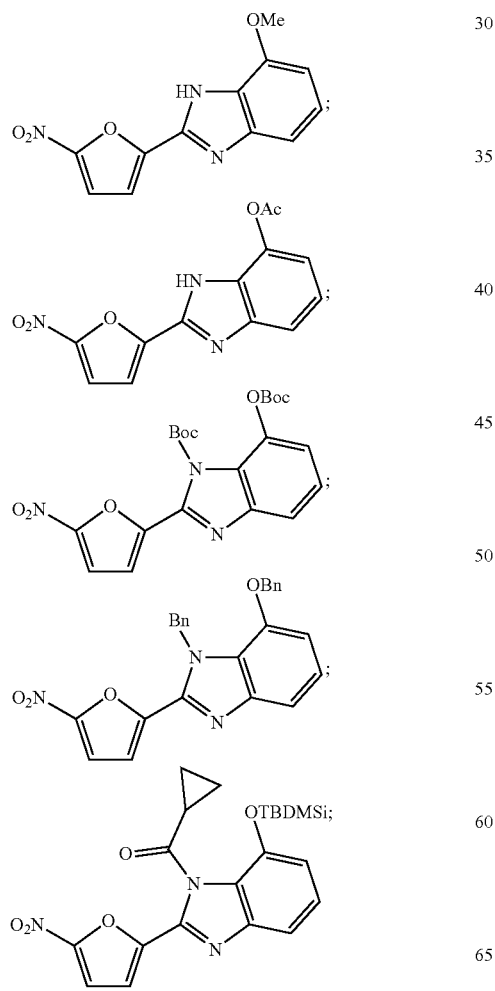

2. The method of claim 1, wherein the compound is:

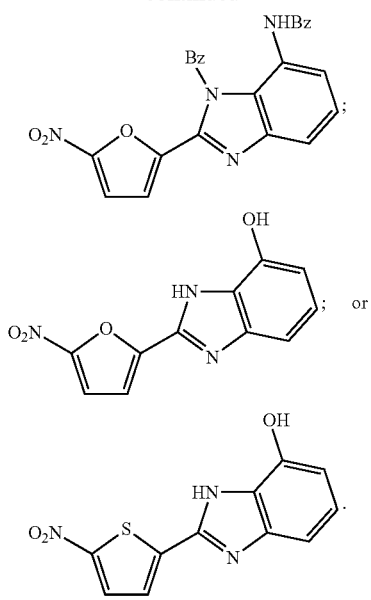

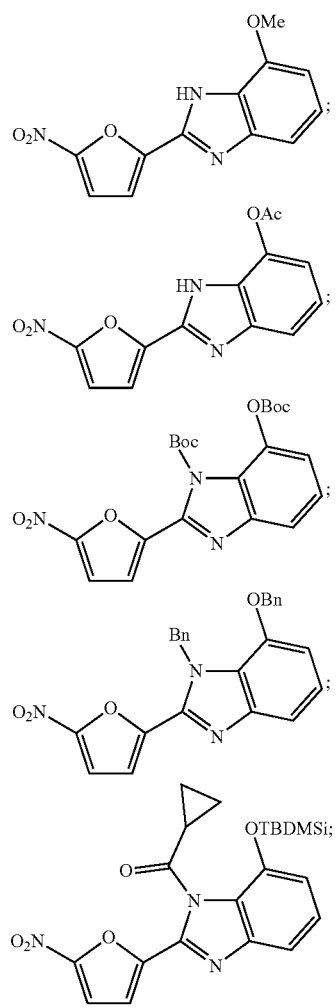

-continued
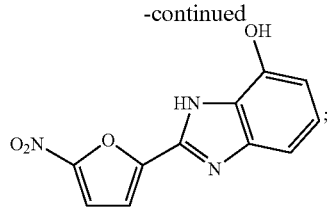; or
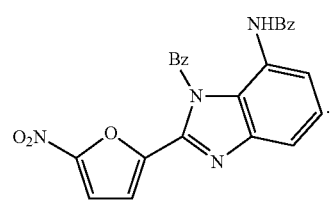.
3. The method of claim 1, wherein the compound is:
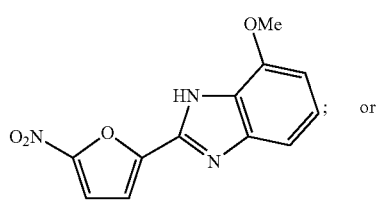; or
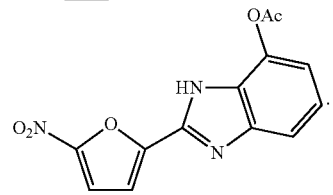.
4. The method of claim 1, wherein the compound is:
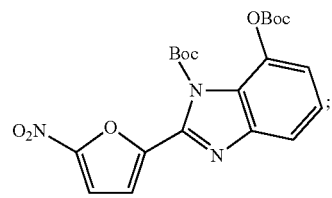;
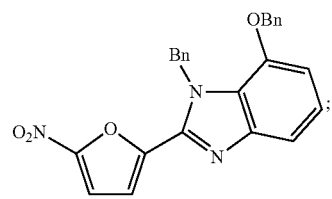;
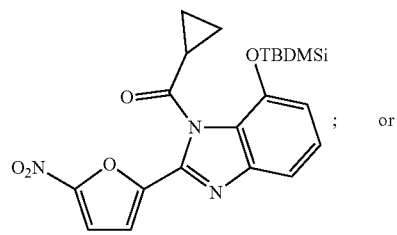; or
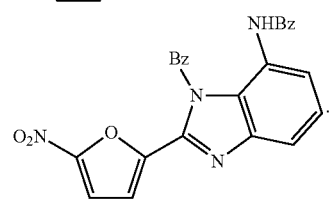.
* * * * *